United States Patent [19]
Hirata et al.

[11] Patent Number: 5,883,092
[45] Date of Patent: Mar. 16, 1999

[54] PYRIMIDINE DERIVATIVES AS ENDOTHELIN ANTAGONISTS

[75] Inventors: Mitsuteru Hirata, Isurugashima; Takeo Deushi, Sayama; Yoshio Takahashi, Iruma; Masahiro Tamura, Higashimurayama; Takeshi Ohshima, Kounosu; Toshiaki Oda, Higashimurayama; Tetsuya Ishikawa, Higashimurayama; Hiroyuki Sonoki, Higashimurayamas; Masami Shiratsuchi, Mushashimurayama, all of Japan

[73] Assignee: Kowa Co., Ltd., Nagoya, Japan

[21] Appl. No.: 29,244

[22] PCT Filed: Sep. 4, 1996

[86] PCT No.: PCT/JP96/02494

§ 371 Date: Mar. 4, 1998

§ 102(e) Date: Mar. 4, 1998

[87] PCT Pub. No.: WO97/09318

PCT Pub. Date: Mar. 13, 1997

[30] Foreign Application Priority Data

Sep. 6, 1995 [JP] Japan .................... 7-228907

[51] Int. Cl.$^6$ ............ C07D 413/04; C07D 403/04; A61K 31/505; A61K 31/535
[52] U.S. Cl. ............... 514/235.8; 514/211; 514/218; 514/255; 514/269; 514/272; 540/544; 540/575; 544/123; 544/298; 544/319; 544/321
[58] Field of Search ............ 514/235.8, 255, 514/269, 272, 211, 218; 544/123, 298, 319, 321; 540/544, 575

[56] References Cited

FOREIGN PATENT DOCUMENTS

| | | | |
|---|---|---|---|
| 658548 | 6/1995 | European Pat. Off. | 544/298 |
| 7-17972 | 1/1995 | Japan | 544/319 |

*Primary Examiner*—Yogendra N. Gupta
*Attorney, Agent, or Firm*—Oblon, Spivak, McClelland, Maier & Neustadt, P.C.

[57] ABSTRACT

The present invention is directed to a pyrimidine derivative of the following formula (1) or a salt of the derivative:

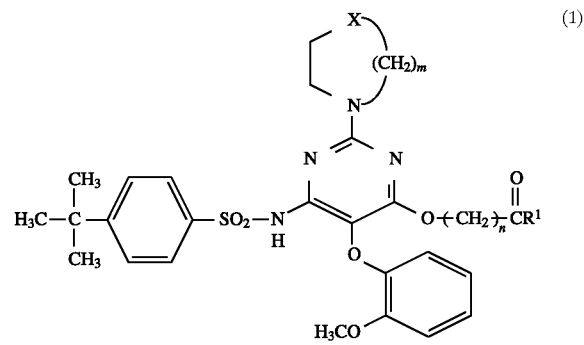

(1)

[wherein $R^1$ represents a hydroxyl group, a lower alkoxy group, a phenyloxy group which may have a substituent, an aralkyloxy group which may have a substituent, or —$NR^2R^3$; X represents an oxygen atom or N—$R^4$; m is 2 or 3; and n is 1 or 2 (wherein each of $R^2$ and $R^3$, which are identical to or different from each other, represents a hydrogen atom, a hydroxyl group, a lower alkyl group which may have a substituent, a phenyl group which may have a substituent, an aralkyl group which may have a substituent, or a heterocyclic group which may have a substituent; $R^4$ represents a lower alkyl group, a phenyl group, a formyl group, or a lower alkoxycarbonyl group)], as well as to a medicine containing the derivative or salt as the active ingredient. The compounds exhibit strong binding inhibitory activity against endothelin having potent vasoconstrictive effect. Therefore, the compounds are effective as remedies for various diseases including circulatory diseases.

12 Claims, No Drawings

PYRIMIDINE DERIVATIVES AS ENDOTHELIN ANTAGONISTS

TECHNICAL FIELD

The present invention relates to novel pyrimidine derivatives and their salts, and to pharmaceuticals containing these compounds as active ingredients.

BACKGROUND ART

Endothelin, having potent vasoconstrictive effect and blood pressure elevating effect, is considered to be a substance that contributes to various diseases and disorders including heart diseases such as ischemic heart infarction, congestive heart failure, arrhythmia, and unstable angina; airway diseases such as asthma; hypertonia such as pulmonary hypertension and renal hypertension; hypofunctions of organs which may occur in association with operation or transplantation thereof; circulatory diseases such as subarachnoid hemorrhage, post-PTCA reconstriction, and vasospasm; kidney diseases such as acute and chronic renal failure; diabetes, hyperlipemia, and other diseases that are accompanied by vascular lesion; arteriosclerosis; liver diseases such as alcohol-induced liver disorders; gastrointestinal disorders such as those of gastric mucosa; bone diseases; prostatic hypertrophy; and urinary disorders; cancer [Saishin-Igaku (may be translated to "Medicine Up-to-date"), 94, 335–431 (1994), Igaku-no-Ayumi (may be translated to "Progress of Medicine"), 168, 675–692 (1994), Igaku-no-Ayumi, 170, 357 (1994)].

It has come to be elucidated that a variety of actions of endothelin are triggered upon binding of endothelin to its receptors in organs of the body, and that the vasoconstriction caused by endothelin is induced by the mediation of at least two different receptors ($ET_A$ and $ET_B$ receptors). Therefore, a compound that prevents endothelin from binding to these two receptors should be useful as a preventive and therapeutic agent for the above-mentioned diseases in which endothelin participates. Heretofore, a number of compounds have been reported as exhibiting endothelin antagonism [J. Med. Chem., 36, 2585 (1993), Nature, 365, 759 (1993), Circulation, 88, 1–316 (1994), Saishin-Igaku, 94, 424–431 (1994), J. Med. Chem. 37, 1553 (1994), and Japanese Patent Application Laid-Open (kokai) Nos. 5-222003, 6-211810, 7-17972, and 8-99961)].

However, no compound has yet been found to exhibit satisfactory endothelin antagonism.

Accordingly, the present invention is directed to the discovery of a compound that has potent endothelin antagonism, as well as to the provision of pharmaceuticals containing such a compound as the active ingredient.

DISCLOSURE OF THE INVENTION

Under the above circumstances, the present inventors carried out careful studies, and found that the pyrimidine derivatives represented by the following formula (1) and their salts exhibit excellent endothelin antagonism and thus are useful as medicines—particularly those for circulatory diseases. The present invention was accomplished based on this finding.

Accordingly, the present invention provides a pyrimidine derivative of the following formula (1) or a salt thereof:

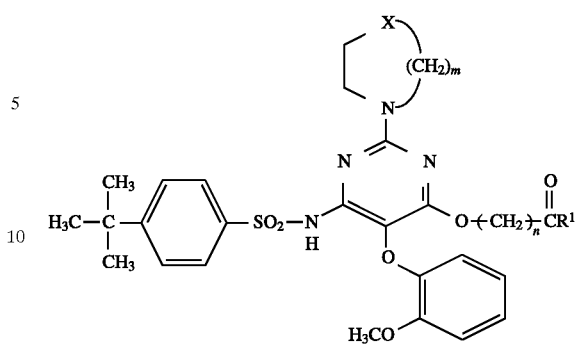

[wherein $R^1$ represents a hydroxyl group, a lower alkoxy group, a phenyloxy group which may have a substituent, an aralkyloxy group which may have a substituent, or —$NR^2R^3$; X represents an oxygen atom or N—$R^4$; m is 2 or 3; and n is 1 or 2 (wherein each of $R^2$ and $R^3$, which are identical to or different from each other, represents a hydrogen atom, a hydroxyl group, a lower alkyl group which may have a substituent, a phenyl group which may have a substituent, an aralkyl group which may have a substituent, or a heterocyclic group which may have a substituent; $R^4$ represents a lower alkyl group, a phenyl group, a formyl group, or a lower alkoxycarbonyl group)].

The present invention also provides a medicine containing a pyrimidine derivative of formula (1) or a salt thereof as an active ingredient.

The present invention also provides a pharmaceutical composition containing a pyrimidine derivative of formula (1) or a salt thereof and a pharmaceutically acceptable carrier.

The present invention also provides use as a medicine of a pyrimidine derivative of formula (1) or a salt thereof.

The present invention also provides a method for treating and preventing diseases induced by endothelin, wherein the method is characterized by administering to a patient an effective amount of a pyrimidine derivative of formula (1) or a salt thereof.

BEST MODE FOR CARRYING OUT THE INVENTION

In the present invention, the term "lower" is used to indicate that the number of carbon atoms is between 1 and 6 inclusive.

In the formula (1), the lower alkoxy groups represented by $R^1$ include linear, branched, or cyclic alkoxy groups having 1–6 carbon atoms, examples of which include methoxy, ethoxy, n-propoxy, isopropoxy, n-butoxy, isobutoxy, sec-butoxy, tert-butoxy, n-pentoxy, n-hexyloxy, cyclopropyloxy, cyclopentyloxy, and cyclohexyloxy.

The phenyloxy groups which may have substituents and which are represented by $R^1$ include phenyloxy groups which may be substituted by alkyl groups having 1–6 carbon atoms, alkoxy groups having 1–6 carbon atoms, or halogen atoms. Specific examples of such phenyloxy groups include methylphenyloxy, ethylphenyloxy, isopropylphenyloxy, methoxyphenyloxy, ethoxyphenyloxy, chlorophenyloxy, bromophenyloxy, and fluorophenyloxy.

The aralkyloxy groups which may have substituents and which are represented by $R^1$ include phenylalkyloxy groups, naphthylalkyloxy groups, biphenylalkyloxy groups, and indanyloxy groups. These groups may be substituted by hydroxy, C1–C6 alkyl, C1–C6 alkoxy, C1–C3 alkylenedioxy, halogen, nitro, trifluoromethyl, or cyano groups. Examples of the alkyl moieties of the aralkyloxy groups include C1–C6 alkyl groups. The aralkyloxy groups may be substituted by one to three groups of substituents. These substituents may be substituted at either the aryl moiety or the alkyl moiety. Specific examples of the aralkyloxy groups which may have substituents include benzyloxy, phenethyloxy, phenylpropoxy, naphthylmethoxy, naphthylethoxy, biphenylmethoxy, and indan-1-yloxy groups, and these groups may be substituted by one to three groups selected from among chloro, fluoro, methoxy, ethoxy, methyl, ethyl, nitro, cyano, and trifluoromethyl groups.

In the lower alkyl groups which may have substituents and which are represented by $R^2$ or $R^3$, the alkyl moieties include linear, branched, or cyclic alkyl groups having 1–6 carbon atoms, examples of which include methyl, ethyl, n-propyl, isopropyl, n-butyl, isobutyl, sec-butyl, tert-butyl, n-pentyl, n-hexyl, cyclopropyl, cyclopentyl, and cyclohexyl. The alkyl moieties may be substituted by one or more (in a total of one to three) hydroxyl groups and halogen atoms. Examples of the alkyl groups substituted by the above-mentioned groups include chloroethyl, bromoethyl, chloropropyl, bromopropyl, chlorobutyl, bromobutyl, hydroxyethyl, hydroxypropyl, hydroxybutyl, and chlorohydroxypropyl.

In the formula (1), examples of the phenyl group which may have a substituent and which is represented by $R^2$ or $R^3$ include phenyl groups which may be substituted by C1–C6 alkyl groups, C1–C6 alkoxyl groups, or by halogen atoms. Specific examples of such phenyl groups include methylphenyl, ethylphenyl, isopropylphenyl, methoxyphenyl, ethoxyphenyl, chlorophenyl, bromophenyl, and fluorophenyl.

The aralkyl groups which may have substituents and which are represented by $R^2$ or $R^3$ include phenylalkyl groups, naphthylalkyl groups, biphenylalkyl groups, and indanyl groups. These groups may be substituted by hydroxy, C1–C6 alkyl, C1–C6 alkoxy, C1–C3 alkylenedioxy, halogen, nitro, trifluoromethyl, or cyano groups. Examples of the alkyl moieties of the aralkyl groups include C1C6 alkyl groups, which may one to three substituents, at either the aryl moiety or the alkyl moiety. Specific examples of the aralkyl groups which may have substituents include benzyl, phenethyl, phenylpropyl, naphthylmethyl, naphthylethyl, biphenylmethyl, and indan-1-yl groups. These groups may be substituted by one to three groups selected from among chloro, fluoro, methoxy, ethoxy, methyl, ethyl, nitro, cyano, and trifluoromethyl groups.

Examples of the heterocyclic groups which may have substituents and which are represented by $R^2$ or $R^3$ include furyl groups, thienyl groups, pyrazolyl groups, thiazolyl groups, thiadiazolyl groups, imidazolyl groups, pyridyl groups, pyrimidinyl groups, and pyrazinyl groups. These groups may be substituted by C1–C6 alkyl groups, C1–C6 alkoxyl groups, C1–C6 haloalkyl groups, or halogen atoms. Specific examples include furyl groups, thienyl groups, pyrazolyl groups, thiazolyl groups, pyridyl groups, pyrimidinyl groups, and pyrazinyl groups. These groups may be substituted by groups selected from among methyl, ethyl, methoxy, ethoxy, chloro, fluoro, and trifluoromethyl groups.

In the formula (1), the lower alkyl groups which may have substituents and which are represented by $R^4$ include linear, branched, or cyclic alkyl groups having 1–6 carbon atoms, examples of which include methyl, ethyl, n-propyl, isopropyl, n-butyl, isobutyl, sec-butyl, tert-butyl, n-pentyl, n-hexyl, cyclopropyl, cyclopentyl, and cyclohexyl. The lower alkoxycarbonyl groups include linear or branched alkoxycarbonyl groups having 2–7 carbon atoms, examples of which include methoxycarbonyl, ethoxycarbonyl, and tert-butoxycarbonyl.

The salts of the compound (1) of the present invention are not particularly limited as long as they are pharmaceutically acceptable. Examples of the salts include mineral acid salts such as hydrochlorides and sulfates; organic acid salts such as acetates, oxalates, and citrates; alkali metal salts such as sodium salts and potassium salts; alkaline earth metal salts such as calcium salts and magnesium salts; and salts of organic bases such as 1,8-diazabicyclo[5.4.0]undec-7-ene (DBU) salts.

Also, the compound (1) of the present invention encompasses its hydrates and solvates.

The compound (1) of the present invention may be prepared in accordance with the following reaction scheme.

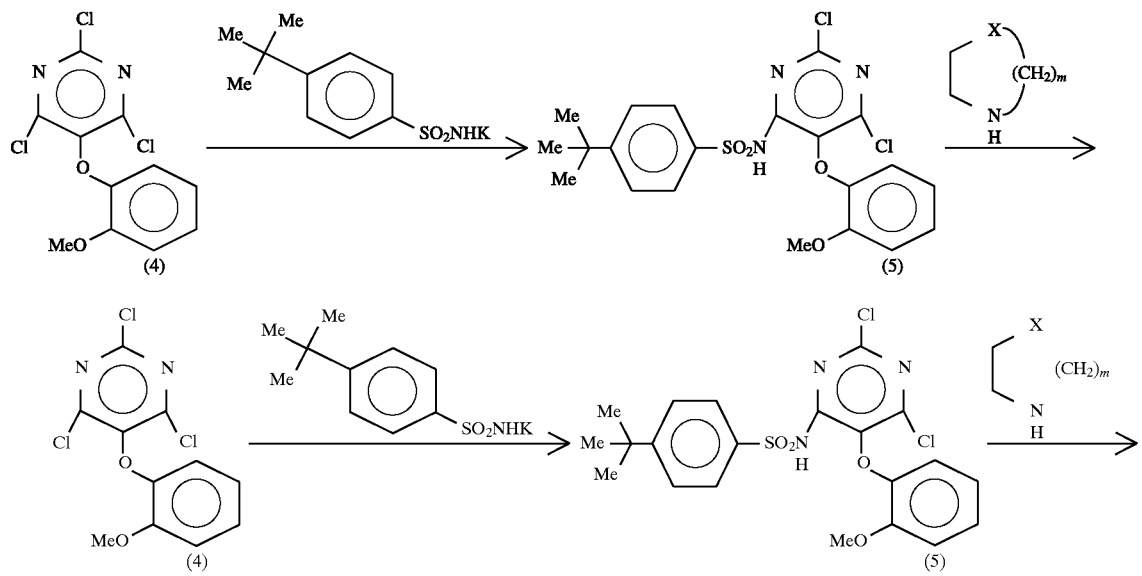

-continued
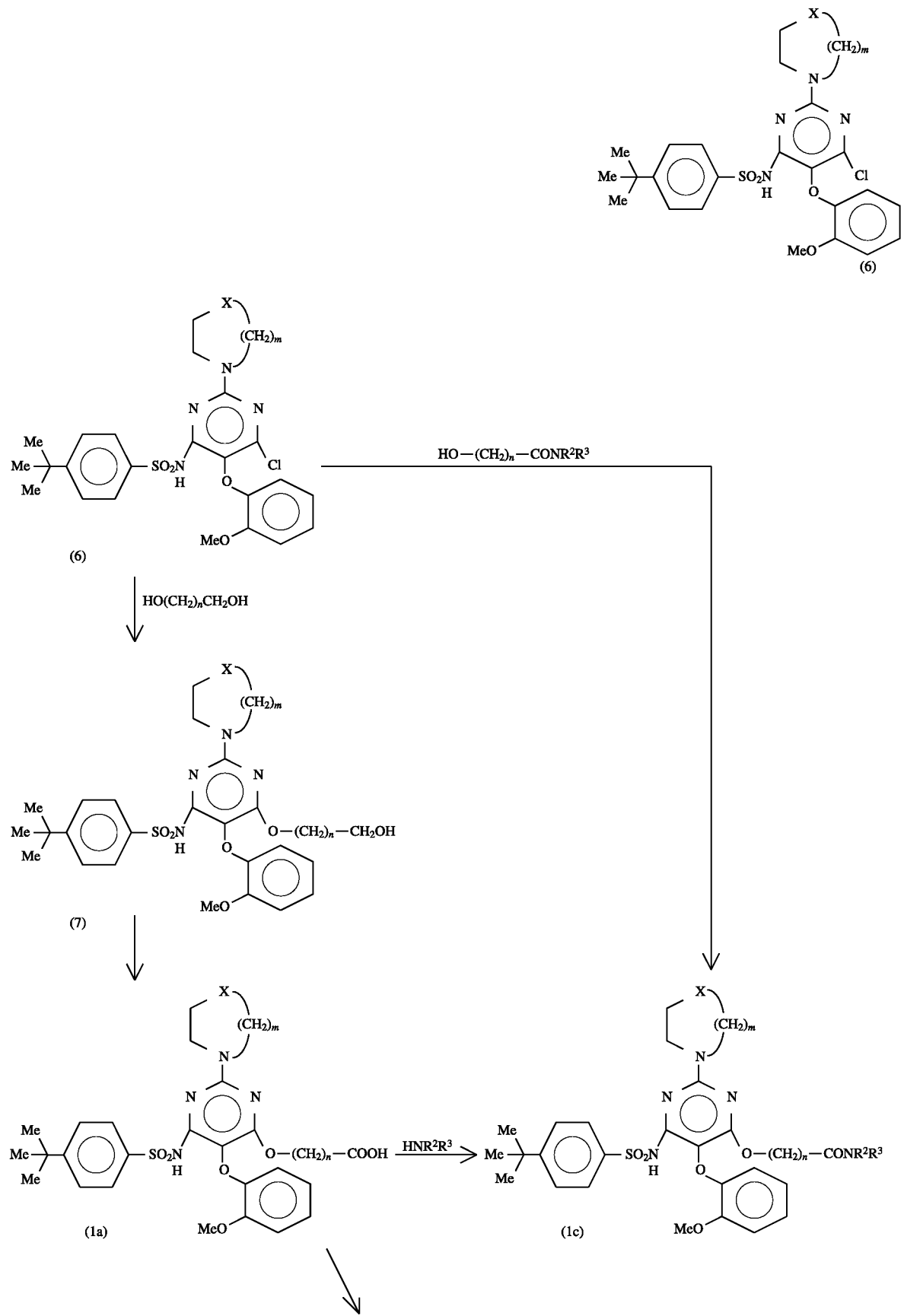

[wherein $R^2$, $R^3$, X, m, and n have the same meanings as defined above, $R^{1a}$ represents a lower alkoxy group, the substituted or unsubstituted phenyloxy group, or the substituted or unsubstituted aralkyloxy group defined with reference to $R^1$].

Briefly, the compound (2) is reacted with urea to obtain the compound (3), which is subsequently reacted with phosphorus oxychloride to obtain the compound (4). The thus-obtained compound (4) is reacted with potassium 4-t-butylbenzenesulfonamide to afford the common intermediate compound (5). The compound (6) is obtained through reaction of the compound (5) and a cyclic amine compound. The compound (6) is reacted with glycol [$HO(CH_2)_nCH_2OH$] to obtain a compound (7), which is subsequently oxidized to afford the compound of the present invention (1a). Esterification of the compound (1a) yields the compound (1b) of the present invention, whereas reaction between the compound (1a) and an amine [$HNR^2R^3$] yields the compound (1c) of the present invention. The compound (1c) is also obtained through reaction of the compound (6) and hydroxyfatty acid amides [$HO(CH_2)_nCONR^2R^3$]. A known method is applicable to reactions in transformation from the compound (2) to the compound (5). Method for obtaining the compound (6) from the compound (5):

The compound (5) is reacted with a cyclic amine compound without use of any solvent or in a solvent such as N,N-dimethylformamide (DMF) and dimethylsulfoxide (DMSO), optionally in the presence of a base such as sodium, sodium hydride, potassium, potassium hydride, potassium tert-butoxide, and potassium carbonate to obtain the compound (6). Method for obtaining the compound (7) from the compound (6):

The compound (6) is reacted with glycol in a solvent such as DMF and DMSO or without use of any solvent, in the presence of a base such as sodium, sodium hydride, potassium, potassium hydride, and potassium tert-butoxide to obtain the compound (7). Method for obtaining the compound (1c) of the present invention from the compound (6):

The compound (6) is reacted with a hydroxyfatty acid amide in the presence of a base such as sodium, sodium hydride, potassium hydride, potassium tert-butoxide, and potassium carbonate to obtain the compound (1c) of the present invention. Method for obtaining the compound (1a) of the present invention from the compound (7):

The compound (7) is oxidized in a polar solvent such as DMF and acetone through use of an oxidizing agent such as chromate typified by pyridinium dichromate (PDC) and the Jones reagent, ruthenium chloride-sodium periodide; etc. Method for obtaining the compound (1b) of the present invention from the compound (1a) of the present invention:

The compound (1a) of the present invention may be esterified by use of the following materials or methods: (1) use of an acid catalyst (e.g., sulfuric acid, hydrochloric acid, p-toluenesulfonic acid), (2) use of a dehydration-condensing agent (use of a dehydration-condensing agent such as dicyclohexylcarbodiimide (DCC), 1-(3-dimethylaminopropyl)-3-ethylcarbodiimide (WSC), etc. in the presence or absence of dimethylaminopyridine), (3) a method via an acid chloride by use of thionyl chloride, oxalyl chloride, etc., (4) a method via a mixed acid anhydride by use of ethyl chlorocarbonate, isobutyl chlorocarbonate, etc., or (5) a method in which the alcohol moiety is activated with thionyl chloride, etc. Method for obtaining the compound (1c) of the present invention from the compound (1a) of the present invention:

The compound (1a) of the present invention may be amidated by use of the following materials or methods: (a) use of a dehydration-condensing agent such as dicyclohexylcarbodiimide (DCC), 1-(3-dimethylaminopropyl)-3-ethylcarbodiimide (WSC), etc., (b) a method via an active ester (a phenyl ester such as p-nitrophenyl ester, N-hydroxybenzotriazol ester, N-hydroxysuccimide ester, etc.) produced by use of the above-mentioned dehydration-condensing agent, (c) a method via an acid chloride by use of thionyl chloride, oxalyl chloride, etc., (d) a method via a mixed acid anhydride by use of ethyl chlorocarbonate, isobutyl chlorocarbonate, etc., (e) a method in which a Woodward K reagent is used, or (f) a method in which a reagent ordinarily used for amidation (such as N-ethyl-2'-hydroxybenzoisoxazolium trifluoroborate, N-ethyl-5-phenylisoxazolium-3'-sulfonate, 1-ethoxycarbonyl-2-ethoxy-1,2-dihydroxyquinoline, benzotriazolyl-N-hydroxy-trisdimethylaminophosphonium hexafluorophosphate, and diphenylphosphoryl azide) is used.

Typical compounds of the formula (1) of the present invention are shown in the following Table 1. In the Table, Me stands for methyl, Et stands for ethyl, Ph stands for phenyl, $^i$Pr stands for isopropyl, and $^t$Bu stands for tert-butyl.

TABLE 1

[Structure: a compound with a tert-butyl-substituted phenylsulfonamide attached to a pyrimidine core (substituent A at one position), with a 2-methoxyphenoxy group and an $O(CH_2)_n$-C(=O)-$R^1$ ester/amide chain]

| Ex. | A | $R^1$ | n |
|---|---|---|---|
| 1 | morpholino (O-containing 6-membered ring with N) | —OH | 2 |
| 2 | morpholino | —NH—(2-isopropylphenyl) | 2 |
| 3 | morpholino | —NH—(pyridyl) | 2 |
| 4 | N-phenylpiperazino | —OH | 2 |

TABLE 1-continued
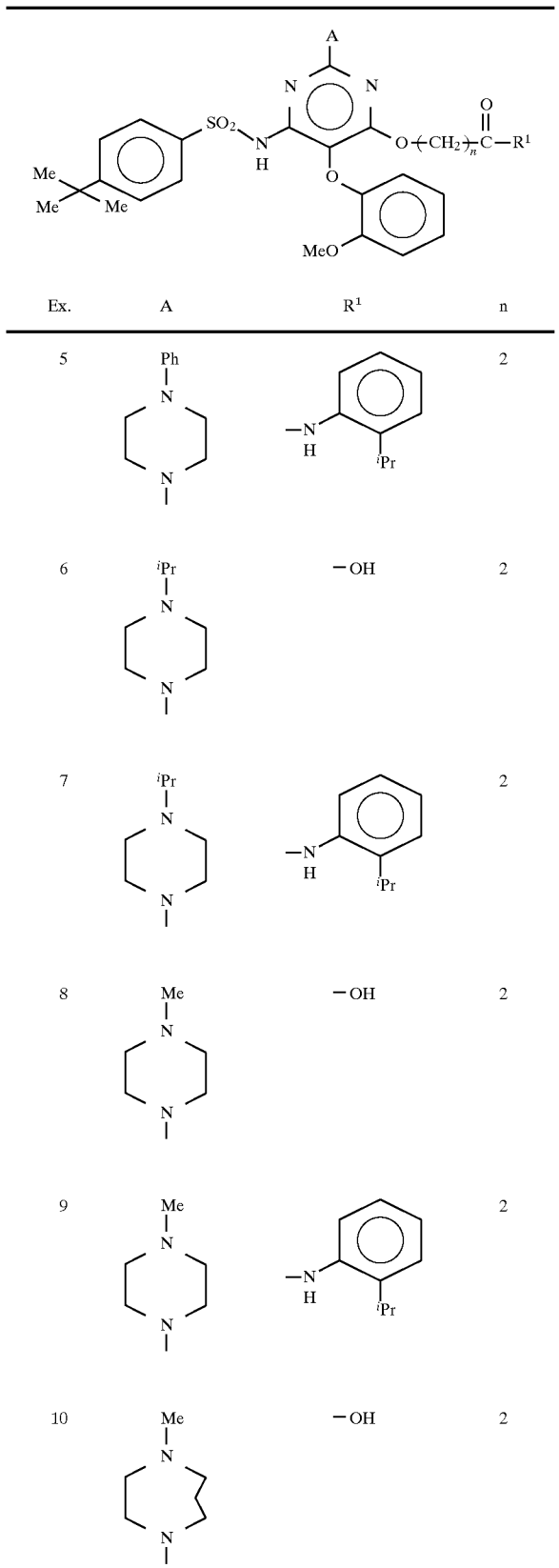
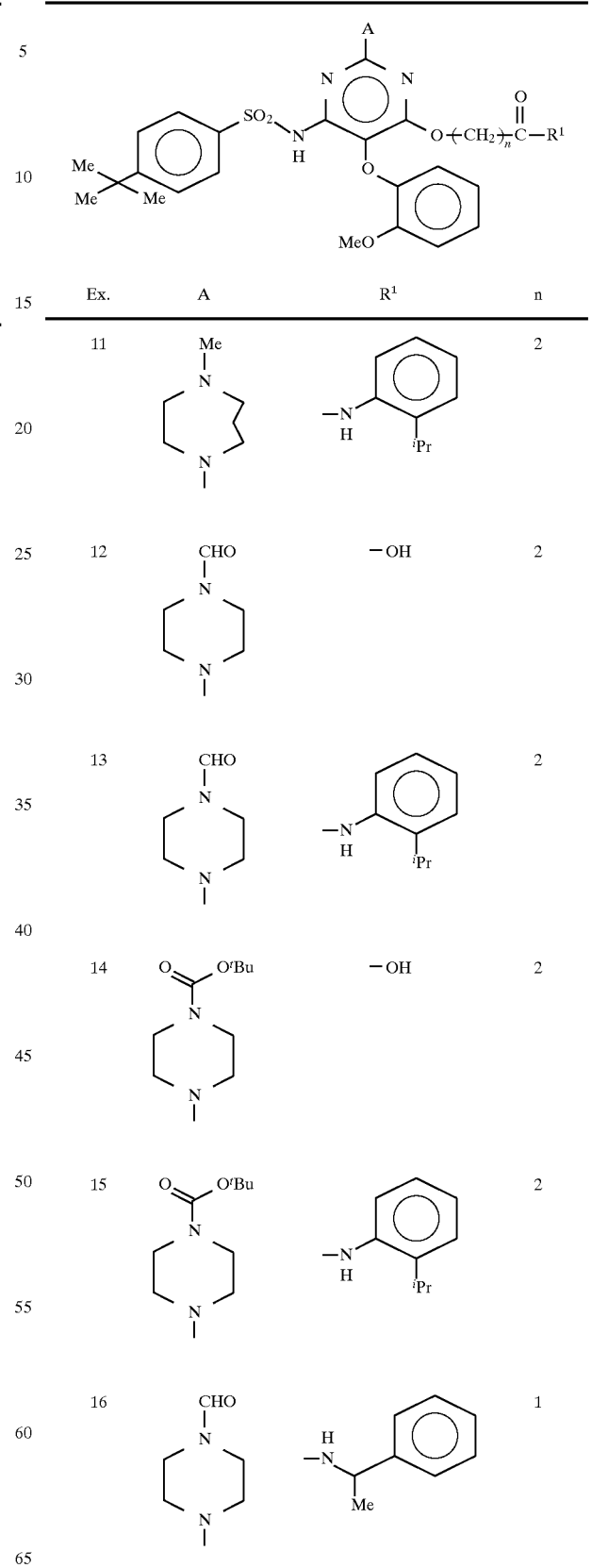

TABLE 1-continued

[Structure: 4-t-butylphenyl-SO2-NH-pyrimidine(A)-O-(CH2)n-C(=O)-R1, with 2-methoxyphenoxy substituent]

| Ex. | A | R¹ | n |
|-----|---|----|----|
| 17 | morpholino (O-linked ring with N) | -NH-C6H4-Et (ortho) | 2 |

TABLE 2

[Same core structure as Table 1]

| Ex. | A | R¹ | n |
|-----|---|----|----|
| 18 | morpholino | -NH-(2,6-dimethylphenyl) | 2 |
| 19 | morpholino | -NH-(2-methoxyphenyl) | 2 |
| 20 | morpholino | -NH-(4-iPr-phenyl) | 2 |
| 21 | morpholino | -NH-(3-iPr-phenyl) | 2 |
| 22 | morpholino | -OMe | 2 |
| 23 | morpholino | -O-CH2-C6H5 | 2 |

The pyrimidine derivative (1) of the present invention or a salt thereof, after being processed together with a pharmaceutically acceptable carrier according to a customary method, may be formed into various peroral or parenteral pharmaceutical compositions of a solid type, semi-solid type, or liquid type.

Examples of peroral preparations include tablets, pills, granules, soft and hard capsules, powders, fine granules, powders, emulsions, syrups, pellets, and elixirs. Examples of parenteral preparations include injections, instillations, transfusions, ointments, lotions, tonics, sprays, suspensions, oils, emulsions, and suppositories. Pharmaceutically acceptable carriers which may be used in the pharmaceutical composition of the present invention are not particularly limited, and if necessary, the following materials are added; surfactants, vehicles, coloring agents, odor improving agents, preservatives, stabilizers, buffers, suspending agents, isotonic agents, etc.

The amount of administration of the pyrimidine derivative (1) or a salt thereof varies in accordance with the identity of the compound, the disease which is to be treated or prevented, manner of administration, age and symptoms of the patient, duration of treatment, etc. In the case of parenteral administration, the amount of administration is preferably between 0.01 and 30 mg/kg, more preferably 0.1–10 mg/Kg for subcutaneous, intravenous, intramuscular, or rectal administration. In the case of peroral administration, the compound is preferably administered in an amount of 0.01–100 mg/kg, more preferably 0.3–30 mg/kg.

EXAMPLES

The present invention will next be described in more detail by way of examples, which should not be construed as limiting the invention.

Synthesis Example 1

Synthesis of 4-t-butyl-N-[2,6-dichloro-5-(2-methoxyphenoxy)-4-pyrimidinyl]benzenesulfonamide (5)

1) Sodium (3.2 g; 160 mmol) was dissolved in ethanol (200 ml). Diethyl (2-methoxyphenoxy)malonate (2) (11.2 g; 160 mmol) and urea (2.6 g; 44 mmol) were added to the mixture while being cooled on ice. The mixture was stirred for 4 hours under reflux. After being cooled, ethanol was evaporated, and the residue was dissolved in a small amount of water and made acidic with hydrochloric acid. The mixture was allowed to stand overnight at room temperature. The crystals that precipitated were collected by filtration and dried, to thereby obtain 7.1 g of 5-(2-methoxyphenoxy)-pyrimidine-2,4,6-trione (3). Phosphorus oxychloride (70 ml) and y-collidine (14 ml) were added to this compound and the mixture was stirred for 10 hours under reflux with heat. After phosphorus oxychloride was evaporated, the residue was added to ice-water and the mixture was extracted with ethyl acetate. The reaction mixture was washed with water and dried over anhydrous sodium sulfate, evaporated, and purified by silica gel column chromatography (ethyl acetate: hexane=1:2), to thereby obtain 4.8 g (yield: 39%) of 5-(2-methoxyphenoxy)-2,4,6-trichloropyrimidine (4) as a colorless solid.

$^1$H-NMR(CDCl$_3$, ppm, TMS): 3.86(3H, s), 6.73(1H, dd, J=1.5, 8.1 Hz), 6.90(1H, dt, J=1.5, 8.1 Hz), 7.00(1H, dd, J=1.5, 7.3 Hz), 7.13(1H, dt, J=1.5, 7.3 Hz)

2) 5-(2-Methoxyphenoxy)-2,4,6-trichloropyrimidine (4) (4.8 g; 15.6 mmol) was dissolved in dimethyl sulfoxide (45 ml). Potassium 4-t-butylbenzenesulfonamide (8.0 g; 32 mmol) was added to the mixture while being cooled on ice, and the mixture was stirred for 30 minutes at room temperature. The reaction mixture was poured into water, made acidic with hydrochloric acid, and extracted with ethyl acetate, washed with water, dried over anhydrous sodium sulfate, and evaporated. The residue was recrystallized from ether, to thereby obtain 4.9 g (yield: 65%) of the title compound as colorless needles.

$^1$H-NMR(CDCl$_3$, ppm, TMS): 1.35(9H, s), 3.92(3H, s), 6.78(1H, dd, J=1.7, 8.3 Hz), 6.89(1H, dt, J=1.7, 7.3 Hz), 7.03(1H, dd, J=1.7, 8.3 Hz), 7.13(1H, dt, J=1.7, 7.3 Hz), 7.51(2H, d, J=8.8 Hz), 7.96(2H, d, J=8.8 Hz) IR(KBr)cm$^{-1}$: 3220, 2954, 1549, 1350, 1179

Synthesis Example 2

Synthesis of 4-t-butyl-N-[6-chloro-5-(2-methoxyphenoxy)-2-morpholino-4-pyrimidinyl] benzenesulfonamide 4-t-Butyl-N-[2,6-dichloro-5-(2-methoxyphenoxy)-4-pyrimidinyl]benzenesulfonamide (5) (482 mg; 1.0 mmol) was dissolved in dimethyl sulfoxide (5 ml). Morpholine (175 mg; 2.0 mmol) was added to the solution, and the resultant mixture was stirred overnight at 100° C. After being cooled, the reaction mixture was poured into water, made acidic with hydrochloric acid, and extracted with ethyl acetate, being washed with water, dried over anhydrous sodium sulfate, and evaporated. The residue was purified by silica gel column chromatography (ethyl acetate:hexane= 1:2), to thereby obtain 240 mg (yield: 45%) of the title compound as a white powder.

$^1$H-NMR(CDCl$_3$, ppm, TMS): 1.33(9H, s), 3.64(8H, m), 4.04(3H, s), 6.88(1H, dt, J=1.5, 8.1 Hz), 6.97(1H, dd, J=1.7, 8.1 Hz), 7.04(1H, dd, J=1.5, 8.1 Hz), 7.14(1H, dt, J=1.7, 8.1 Hz), 7.45(2H, d, J=8.8 Hz), 7.80(2H, d, J=8.8 Hz), 8.69(1H, s) IR(KBr)cm$^{-1}$: 2965, 1605, 1540, 1495, 1440, 1340, 1115, 955, 755

Synthesis Example 3

Synthesis of 4-t-butyl-N-[6-(3-hydroxypropyloxy)-5-(2-methoxyphenoxy)-2-morpholino-4-pyrimidinyl]-benzenesulfonamide 1,3-Propanediol (580 mg) was dissolved in dimethyl sulfoxide (15 ml). Sodium hydride (297 mg) and 4-t-butyl-N-[6-chloro-5-(2-methoxyphenoxy)-2-morpholino-4-pyrimidinyl]benzenesulfonamide (1.1 g) were added to the solution. The resultant mixture was stirred for 4 hours at 120° C. Ethyl acetate was added to the reaction mixture, followed by successive washing with 0.5N-HCl, water, and saturated brine. The organic layer was dried over anhydrous sodium sulfate, and evaporated. The residue was purified by silica gel column chromatography (chloroform:methanol= 50:1), to thereby obtain 802 mg (yield: 68%) of the title compound as a white powder.

$^1$H-NMR(CDCl$_3$, ppm, TMS): 1.33(9H, s), 1.88(2H, qn, J=6.0 Hz), 3.52–3. 67(10H, m), 4.01(3H, s), 4.41(2H, t, J=6.0 Hz), 6.84(1H, dt, J=1.7, 8.1 Hz), 6.94(1H, dd, J=1.7, 8.1 Hz), 6.99(1H, dd, J=1.7, 8.2 Hz), 7.08(1H, dt, J=1.7, 8.2 Hz), 7.45(2H, d, J=8.8 Hz), 7.86(2H, d, J=8.8 Hz), 8.52(1H, s) IR(KBr)cm$^{-1}$: 3495, 2965, 1615, 1560, 1500, 1440, 1170, 1110, 1085, 755.

Example 1

Synthesis of 3-[6-(4-t-butylphenyl-sulfonylamino)-5-(2-methoxyphenoxy)-2-morpholino-4-pyrimidinyloxy]propionic acid 4-t-Butyl-N-[6-(3-hydroxypropyloxy)-5-(2-methoxyphenoxy)-2-morpholino-4-pyrimidinyl]-benzenesulfonamide (800 mg) was dissolved in dimethylformamide (40 ml). Pyridinium dichromate (2.63 g) was added to the solution, and the resultant mixture was stirred for 14 hours at room temperature. Ethyl acetate was added to the reaction mixture, followed by successive washing with 0.5N-HCl, water, and brine. The organic layer was dried over anhydrous sodium sulfate and, evaporated. The residue was purified by silica gel column chromatography (chloroform:methanol=25:1), to thereby obtain 128 mg (yield: 16%) of the title compound as a white powder.

$^1$H-NMR(CDCl$_3$, ppm, TMS): 1.32(9H, s), 2.75(2H, t, J=6.4 Hz), 3.52–3.67(8H, m), 4.01(3H, s), 4.53(2H, t, J=6.4 Hz), 6.81(1H, dt, J=1.5, 7.6 Hz), 6.93–7.09(3H, m), 7.44 (2H, d, J=8.6 Hz). 7.84(2H, d, J=8.6 Hz) IR(KBr)cm $^{-1}$: 3210, 2965, 1720, 1615, 1560, 1500, 1440, 1250, 1170, 1110, 1085, 750

Example 2

Synthesis of N-(2-isopropylphenyl)-3-[6-(4-t-butylphenylsulfonylamino)-5-(2-methoxyphenoxy)-2-morpholino-4-pyrimidinyloxy]propionamide 3-[6-(4-t-Butylphenylsulfonylamino)-5-(2-methoxyphenoxy)-2-morpholino-4-pyrimidinyloxy] propionic acid (80 mg) was dissolved in dimethylformamide-methylene chloride (1:1, 6 ml). N-Hydroxybenzotriazole·H$_2$O (42.2 mg), 2-isopropylaniline (133.2 mg), and 1-(3-dimethylaminopropyl) -3-ethylcarbodiimide-HCl (32.6 mg) were added to the mixture. The reaction mixture was stirred overnight at room temperature. After the solvent was evaporated, ethyl acetate was added. The organic layer was successively washed with sat. aq. NaHCO$_3$, 0.5N-HCl, and brine, was dried over anhydrous sodium sulfate, and evaporated. The residue was purified by silica gel column chromatography (chloroform:methanol=30:1), to thereby obtain 97.2 mg (yield: 100%) of the title compound as a colorless oil.

$^1$H-NMR(CDCl$_3$, ppm. TMS): 1.09(6H, d, J=6.8 Hz), 1.32(9H, s), 2.76(2H, t, J=5.7 Hz), 2.89(1H, sep, J=6.8 Hz), 3.60(8H, m), 3.90(3H, s), 4.66(2H, t, J=5.7 Hz), 6.68(1H, dt, J=1.2, 7.7 Hz), 6.86–7.04(3H, m), 7.10–7.26(3H, m), 7.45

(2H, d, J=8.5 Hz), 7.50(1H, m), 7.82(2H, d, J=8.5 Hz), 8.70(1H, s) IR(KBr)cm$^{-1}$: 2965, 1670, 1615, 1560, 1520, 1500, 1440, 1340, 1250, 1170, 1085, 755

Example 3

Synthesis of N-(2-pyridyl)-3-[6-(4-t-butylphenylsulfonylamino)-5-(2-methoxyphenoxy)-2-morpholino-4- pyrimidinyloxy]propionamide 3-[6-(4-t-Butylphenylsulfonylamino)-5-(2-methoxyphenoxy)-2-morpholino-4-pyrimidinyloxy] propionic acid (121 mg) was dissolved in methylene chloride (0.9 ml). Oxalyl chloride (27 mg) and dimethylformamide (1 droplet) were added, and the mixture was stirred for 30 minutes at room temperature. 2-Aminopyridine (38 mg) was added, and the mixture was stirred overnight at room temperature. After the solvent was evaporated, ethyl acetate was added. The organic layer was successively washed with 0.5N-HCl, sat. aq. NaHCO$_3$, and brine, dried over anhydrous sodium sulfate, and evaporated. The residue was purified by silica gel column chromatography (chloroform:methanol=10:1), to thereby obtain 51 mg (yield: 37%) of the title compound as a white powder.

$^1$H-NMR(CDCl$_3$, ppm, TMS): 1.32(9H, s), 3.53–3.67 (8H, m), 3.95(3H, s), 4.63(1H, t, J=6.1 Hz), 6.62(1H, ddd, J=2.4, 6.6, 8.1 Hz), 6.84–6.97(3H, m), 7.03(1H, ddd, J=1.0, 4.9, 7.3 Hz), 7.44(2H, d, J=8.6 Hz), 7.68(1H, dt, J=2.0, 7.3 Hz), 7.83(2H, d, J=8.6 Hz), 8.14(1H, d, J=8.6 Hz), 8.23(2H, m), 8.68(1H, brs) IR(KBr)cm$^{-1}$: 2965, 1700, 1615, 1560, 1435, 1300, 1170, 1110, 1085, 750

Synthesis Example 4

Synthesis of 4-t-butyl-N-[6-chloro-5-(2-methoxyphenoxy)-2-(4- phenylpiperazinyl)-4-pyrimidinyl]benzenesulfonamide The procedure described in Synthesis Example 2 was repeated by use of 4-t-butyl-N-[2,6-dichloro-5-(2-methoxyphenoxy)-4-pyrimidinyl]benzenesulfonamide (5) and 1-phenylpiperazine, to thereby obtain the title compound.

Synthesis Example 5

Synthesis of 4-t-butyl-N-[6-(3-hydroxypropyloxy)-5-(2-methoxyphenoxy)-2-(4-phenylpiperazinyl)-4-pyrimidinyl]benzenesulfonamide The procedure described in Synthesis Example 3 was repeated by use of 4-t-butyl-N-[6-chloro-5-(2-methoxyphenoxy)-2-(4-phenylpiperazinyl)-4-pyrimidinyl] benzenesulfonamide and 1,3-propanediol, to thereby obtain the title compound as a pale yellow oil.

$^1$H-NMR(CDCl$_3$, ppm, TMS): 1.31(9H, s), 1.90(2H, sep, J=5.9 Hz), 3.13(4H, t, J=4.6 Hz), 3.60(2H, t, J=5.9 Hz), 3.78(4H, t, J=4.6 Hz), 4.45(2H, t, J=5.9 Hz), 6.81–7.11(8H, m), 7.31(1H, d, J=7.3 Hz), 7.47(2H, d, J=8.3 Hz), 7.89(2H, d, J=8.3 Hz)

Example 4

Synthesis of 3-[6-(4-t-butylphenylsulfonylamino)-5-(2-methoxyphenoxy)-2-(4-phenylpiperazinyl)-4-pyrimidinyloxy]propionic acid The procedure described in Example 1 was repeated by use of 4-t-butyl-N-[6-(3-hydroxypropyloxy)-5-(2-methoxyphenoxy)-2-(4-phenylpiperazinyl)-4 -pyrimidinyl] benzenesulfonamide, to thereby obtain the title compound as a pale yellow solid.

$^1$H-NMR(CDCl$_3$, ppm, TMS): 1.31 (9H, s), 2.71 (2H, t, J=5.7 Hz), 3.80–4.11(8H, br), 4.02(3H, s), 4.62(2H, t, J=5.7 Hz), 6.70–7.36(9H, m), 7.51(2H, d, J=8.5 Hz), 7.85(2H, d, J=8.5 Hz), 8.31(1H, s), 9.33(1H, s)

Example 5

Synthesis of N-(2-isopropylphenyl)-3-[6-(4-t-butylphenylsulfonylamino)-5-(2-methoxyphenoxy)-2-(4-phenyl-piperazinyl)-4-pyrimidinyloxy]-propionamide The procedure described in Example 2 was repeated by use of 3-[6-(4-t-butylphenylsulfonylamino)-5-(2-methoxyphenoxy)-2-(4-phenylpiperazinyl)-4-pyrimidinyloxy]propionic acid and 2-isopropylaniline, to thereby obtain the title compound as a pale yellow oil.

$^1$H-NMR(CDCl$_3$, ppm, TMS): 1.13(6H, d, J=6.3 Hz), 1.31 (9H, s), 2.92(2H, t, J=5.7 Hz), 3.00(1H, sep, J=6.3 Hz), 3.90–4.12(8H, m), 4.02(3H, s), 4.79(2H, t, J=7.5 Hz), 6.87 (1H, t, J=6.0 Hz), 6.96–7.57(11H, m), 7.51 (2H, d, J=8.6 Hz), 7.85(2H, d, J=8.6 Hz)

Synthesis Example 6

Synthesis of 4-t-butyl-N-[6-chloro-2-(4-isopropylpiperazinyl)-5-(2-methoxyphenoxy)-4-pyrimidinyl]-benzenesulfonamide The procedure described in Synthesis Example 2 was repeated by use of 4-t-butyl-N-[2,6-dichloro-5-(2-methoxyphenoxy)-4-pyrimidinyl]benzenesulfonamide (5) and 1-isopropylpiperazine, to thereby obtain the title compound as a pale yellow oil.

$^1$H-NMR(CDCl$_3$, ppm, TMS): 1.12(6H, d, J=6.3 Hz), 1.21(9H, s), 2.63–3.41 (9H, br), 3.76(3H, s), 6.30(1H, dd, J=1.5, 7.8 Hz), 6.73(1H, dt, J=1.5, 7.8 Hz), 6.85(1H, dt, J=1.5, 7.8 Hz); 6.96(1H, dd, J=1.5, 7.8 Hz), 7.36(2H, d, J=8.3 Hz), 7.51(2H, d, J=8.3 Hz)

Synthesis Example 7

Synthesis of 4-t-butyl-N-[6-(3-hydroxypropyloxy)-2-(4-isopropylpiperazinyl)-5-(2-methoxyphenoxy)-4-pyrimidinyl]benzenesulfonamide The procedure described in Synthesis Example 3 was repeated by use of 4-t-butyl-N-[6-chloro-2-(4-isopropyl-piperazinyl)-5-(2-methoxyphenoxy)-4-pyrimidinyl]-benzenesulfonamide and 1,3-propanediol, to thereby obtain the title compound as a pale yellow oil.

$^1$H-NMR(CDCl$_3$, ppm, TMS): 1.06(6H, d, J=6.6 Hz), 1.32(9H, s), 1.88(2H, t, J=6.1 Hz), 2.50(4H, t, J=4.9 Hz), 2.76(1H, Sep, J=6.6 Hz), 3.58(2H, t, J=6.1 Hz), 3.66(4H, t, J=4.9 Hz), 4.00(3H, S), 4.41 (2H, t, J=6.1 Hz), 6.77–7.14 (4H, m), 7.45(2H, d, J=8.7 Hz), 7.87(2H, d, J=8.7 Hz)

Example 6

Synthesis of 3-[6-(4-t-butylphenylsulfonylamino)-2-(4-isopropylpiperazinyl)-5-(2-methoxyphenoxy)-4-pyrimidinyloxy]-propionic acid The procedure described in Example 1 was repeated by use of 4-t-butyl-N-[6-(3-hydroxypropyloxy)-2-(4-isopropylpiperazinyl)-5-(2-methoxyphenoxy)-4-pyrimidinyl]-benzenesulfonamide, to thereby obtain the title compound.

Example 7

Synthesis of N-(2-isopropylphenyl)-3-[6-(4-t-butylphenylsulfonylamino)-2-(4-isopropylpiperazinyl)-5-(2-methoxyphenoxy)-4-pyrimidinyloxy]-propionamide The procedure described in Example 2 was repeated by use of 3-[6-(4-t-butylphenylsulfonylamino)-2-(4-isopropylpiperazinyl-5-(2-methoxyphenoxy)-4-pyrimidinyloxy]propionic acid and 2-isopropylaniline, to thereby obtain the title compound as a pale yellow oil.

$^1$H-NMR(CDCl$_3$, ppm, TMS): 1.12(6H, d, J=6.8 Hz), 1.24(6H, d, J=6.8 Hz), 1.32(9H, s), 2.70(4H, t, J=4.9 Hz), 2.91–3.28(4H, m), 3.31 (4H, t, J=4.9 Hz), 4.03(3H, s), 4.91(2H, t, J=7.1 Hz), 6.60–7.25(8H, m), 7.52(2H, d, J=8.6 Hz), 7.87(2H, d, J=8.6 Hz)

Synthesis Example 8

Synthesis of 4-t-butyl-N-[6-chloro-5-(2-methoxyphenoxy)-2-(4-methylpiperazinyl)-4-pyrimidinyl]benzenesulfonamide The procedure described in Synthesis Example 2 was repeated by use of 4-t-butyl-N-[2,6-dichloro-5-(2-methoxyphenoxy)-4-pyrimidinyl]benzenesulfonamide (5) and N-methylpiperazine, to thereby obtain the title compound as a pale yellow oil.

$^1$H-NMR(CDCl$_3$, ppm, TMS): 1.33(9H, s), 2.31(3H, s), 2.36(4H, t, J=4.6 Hz), 3.68(4H, t. J=4.6 Hz), 4.04(3H, s), 6.88(1H, dt, J=1.5, 6.4 Hz), 6.96(1H, dd, J=1.5, 6.4 Hz), 7.04(1H, dd, J=1.5, 6.5 Hz), 7.11(1H, dt, J=1.5, 6.5 Hz)

Synthesis Example 9

Synthesis of 4-t-butyl-N-[6-(3-hydroxypropyloxy-5-(2-methoxyphenoxy)-2-(4-methylpiperazinyl)-4-pyrimidinyl]benzenesulfonamide The procedure described in Synthesis Example 3 was repeated by use of 4-t-butyl-N-[6-chloro-5-(2-methoxyphenoxy)-2-(4-methylpiperazinyl)-4-pyrimidinyl]benzenesulfonamide and 1,3-propanediol, to thereby obtain the title compound as a pale yellow oil.

$^1$H-NMR(CDCl$_3$, ppm, TMS): 1.32(9H, s), 1.84–1.92 (2H, m), 2.31 (3H, s), 2.36(4H, t, J=4.9 Hz), 3.58(2H, t, J=6.0 Hz), 3.64(4H, t, J=4.9 Hz), 4.01 (3H, s), 4.41 (2H, t, J=6.0 Hz), 6.84(1H, dt, J=1.5, 7.1 Hz), 6.94(1H, dd, J=1.5, 7.1 Hz), 6.99(1H, dd, J=1.5, 7.1 Hz), 7.07(1H, dt, J=1.5, 7.1 Hz), 7.45(2H, d, J=8.6 Hz), 7.87(2H, d, J=8.6 Hz)

Example 8

Synthesis of 3-[6-(4-t-butylphenylsulfonylamino)-5-(2-methoxyphenoxy)-2-(4-methylpiperazinyl)-4-pyrimidinyloxy]propionic acid The procedure described in Example 1 was repeated by use of 4-t-butyl-N-[6-(3-hydroxypropyloxy)-5-(2-methoxyphenoxy)-2-(4-methylpiperazinyl)-4-pyrimidinyl]benzenesulfonamide, to thereby obtain the title compound.

Example 9

Synthesis of N-(2-isopropylphenyl)-3-[6-(4-t-butylphenylsulfonylamino)-5-(2-methoxyphenoxy)-2-(4-methylpiperazinyl)-4-pyrimidinyloxy]-propionamide The procedure described in Example 2 was repeated by use of 3-[6-(4-t-butylphenylsulfonylamino)-5-(2-methoxyphenoxy)-2-(4-methylpiperazinyl)-4-pyrimidinyloxy]propionic acid and 2-isopropylaniline, to thereby obtain the title compound as a pale yellow solid.

$^1$H-NMR(CDCl$_3$, ppm, TMS): 1.13(6H, d, J=6.8 Hz), 1.32(9H, s), 2.32(3H, S), 2.49(4H, t, J=4.9 Hz), 2.90(2H, t, J=5.8 Hz), 2.99(1H, sep, J=6.8 Hz), 3.60(4H, t, J=4.9 Hz), 4.01(3H, s), 4.75(2H, t, J=5. 8 Hz), 6.71–7.15(8H, m), 7.55(2H, d, J=8.7 Hz), 7.88(2H, d, J=8.7 Hz)

Synthesis Example 10

Synthesis of 4-t-butyl-N-[6-chloro-5-(2-methoxyphenoxy)-2-(4-methylhomopiperazinyl)-4-pyrimidinyl]benzenesulfonamide The procedure described in Synthesis Example 2 was repeated by use of 4-t-butyl-N-[2,6-dichloro-5-(2-methoxyphenoxy)-4-pyrimidinyl]benzenesulfonamide (5) and N-methylhomepiperazine, to thereby obtain the title compound as a pale yellow oil.

$^1$H-NMR(CDCl$_3$, ppm, TMS): 1.32(9H, s), 1.98–2.10 (2H, br), 2.45(3H, s), 2.65–2.81(4H, br), 3.61–3.88(4H, br), 4.04(3H, S), 6.87–7.16(4H, m), 7.46(2H, t, J=8.3 Hz), 7.79(2H, d, J=8.3 Hz)

Synthesis Example 11

Synthesis of 4-t-butyl-N-[6-(3-hydroxypropyloxy)-5-(2-methoxyphenoxy)-2-(4-methylhomopiperazinyl)-4-pyrimidinyl]benzenesulfonamide The procedure described in Synthesis Example 3 was repeated by use of 4-t-butyl-N-[6-chloro-5-(2-methoxyphenoxy)-2-(4-methylhomopiperazinyl)-4-pyrimidinyl]benzenesulfonamide and 1,3-propanediol, to thereby obtain the title compound as a pale yellow oil.

$^1$H-NMR(CDCl$_3$, ppm TMS): 1.33(9H s), 1.81–1.99(4H, m) 1.32(9H, s), 2.36(3H, s), 2.44–2.60(4H, br), 3.59(2H, t J=6.1 Hz), 3.64–3.79(4H, br), 4.01(3H, s), 4.43(2H, t, J=6.1 Hz), 6.85(1H, t, J=8.1 Hz), 6.95–7.11(3H, m), 7.46(2H, d, J=8.5 Hz), 7.86(2H, d, J=8.5 Hz)

Example 10

Synthesis of 3-[6-(4-t-butylphenyl-sulfonylamino)-5-(2-methoxyphenoxy)-2-(4-methylhomopiperazinyl)-4-pyrimidinyloxy] propionic acid The procedure described in Example 1 was repeated by use of 4-t-butyl-N-[6-(3-hydroxypropyloxy)-5-(2-methoxyphenoxy)-2-(4-methylhomopiperazinyl)-4-pyrimidinyl]benzenesulfonamide, to thereby obtain the title compound.

Example 11

Synthesis of N-(2-isopropylphenyl)-3-[6-(4-t-butylphenylsulfonylamino)-5-(2-methoxyphenoxy)-2-(4-methylhomopiperazinyl)-4-pyrimidinyloxy] propionamide.

The procedure described in Example 2 was repeated by use of 3-[6-(4-t-butylphenylsulfonylamino)-5-(2-methoxyphenoxy)-2-(4-methylhomopiperazinyl)-4-pyrimidinyloxy]propionic acid and 2-isopropylaniline, to thereby obtain the title compound as a pale yellow oil.

$^1$H-NMR(CDCl$_3$, ppm, TMS): 1.13(6H, d, J=6.8 Hz), 1.33(9H, S), 1.85–2.01(2H, br), 2.36(3H, s), 2.49–2.89(6H, m), 2.99(1H, sep, J=6.8 Hz), 3.60–3.85(4H, br), 4.00(3H, s), 4.75(2H, t, J=5.9 Hz), 6.89–7.25(8H, m), 7.48(2H, d, J=8.5 Hz), 7.86(2H, d, J=8.5 Hz)

Synthesis Example 12

Synthesis of 4-t-butyl-N-[6-chloro-2-(4-formylpiperazinyl)-5-(2-methoxyphenoxy)-4-pyrimidinyl]-benzenesulfonamide The procedure described in Synthesis Example 2 was repeated by use of 4-t-butyl-N-[2,6-dichloro-5-($^2$-methoxyphenoxy)-4-pyrimidinyl]benzenesulfonamide (5) and 1-formylpiperazine, to thereby obtain the title compound as a pale yellow oil.

$^1$H-NMR(CDCl$_3$, ppm, TMS): 1.33(9H, s), 3.33(2H, t, J=4.9 Hz), 3.50(2H, t, J=4.9 Hz), 3.65(2H, t, J=4.9 Hz), 3.72(2H, t, J=4.9 Hz), 4.04(3H, s), 6.89(1H, dt, J=1.5, 7.1 Hz), 6.98(1H, dd, J=1.5, 7.1 Hz), 7.05(1H, dd, J=1.5, 7.1 Hz), 7.15(1H, dt, J=1.5, 7.1 Hz), 7.47(2H, d, J=8.5 Hz), 7.81(2H, d, J=8.5 Hz), 8.12(1H, s)

Synthesis Example 13

Synthesis of 4-t-butyl-N-[2-(4-formylpiperazinyl)-6-(3-hydroxypropyloxy)-5-(2-methoxyphenoxy)-4-pyrimidinyl]benzenesulfonamide The procedure described in Synthesis Example 3 was repeated by use of 4-t-butyl-N-[6-chloro-2-(4-formylpiperazinyl)-5-(2-methoxyphenoxy)-4 -pyrimidinyl]benzenesulfonamide and 1,3-propanediol, to thereby obtain the title compound as a pale yellow solid.

$^1$H-NMR(CDCl$_3$, ppm, TMS): 1.31 (9H, s), 1.87(1H, m), 3.03(4H, brs), 3.57(2H, t, J=5.9 Hz), 3.82(4H, brs), 3.99(3H, s), 4.38(2H, t, J=5.9 Hz), 6.83(1H, dt, J=1.5, 8.1 Hz), 6.92(1H, dd, J=1.5, 8.1 Hz), 6.98(1H, dd, J=1.5, 8.1 Hz), 7.06(1H, dt, J=1.5, 8.1 Hz), 7.45(2H, d, J=8.5 Hz), 7.82(2H, d, J=8.5 Hz)

Synthesis Example 14

Synthesis of 4-t-butyl-N-[2-(4-formylpiperazinyl)-6-(3-hydroxypropyloxy)-5-(2-methoxyphenoxy)-4-pyrimidinyl]benzenesulfonamide 4-t-Butyl-N-[6-(3-hydroxypropyloxy)-5-(2-methoxyphenoxy)-2-piperazinyl-4-pyrimidinyl]-benzenesulfonamide (80 mg; 0.14 mmol), WSC·HCl (61.6 mg; 0.28 mmol), N-hydroxybenzotriazole (75.6 mg; 0.56 mmol), and formic acid (6.5 mg; 0.15 mmol) were dissolved in dimethylformamide-methylene chloride (1:1, 1 ml). The mixture was stirred overnight at room temperature. The reaction mixture was poured into water, made acidic with hydrochloric acid, and extracted with ethyl acetate. The organic layer was washed with water, dried over anhydrous sodium sulfate, and evaporated. The residue was purified by silica gel column chromatography (chloroform:methanol= 15:1), to thereby obtain 20 mg (yield: 23.8%) of the title compound as a pale yellow oil.

$^1$H-NMR(CDCl$_3$, ppm, TMS): 1.33(9H, s), 1.82–1.95 (2H, m), 3.29(2H, t, J=4.9 Hz), 3.47(2H, t, J=4.9 Hz), 3.53–3.78(6H, m), 4.01(3H, s), 4.41 (2H, t, J=6.1 Hz), 6.82–7.11 (4H, m), 7.47(2H, d, J=8.8 Hz), 7.86(2H, d, J=8.8 Hz), 8.10(1H, s)

Example 12

Synthesis of 3-[6-(4-t-butylphenylsulfonylamino)-2-(4-formylpiperazinyl)-5-(2-methoxyphenoxy)-4-pyrimidinyloxy]-propionic acid The procedure described in Example 1 was repeated by use of 4-t-butyl-N-[2-(4-formylpiperazinyl)-6-(3-hydroxypropyloxy)-5-(2-methoxyphenoxy)-4-pyrimidinyl] benzenesulfonamide, to thereby obtain the title compound as a pale yellow solid.

$^1$H-NMR(CDCl$_3$, ppm, TMS) 1.31 (9H, s), 2.78(2H, t, J=6.6 Hz), 3.27(2H, t, J=6.3 Hz), 3.41 (2H, t, J=6.3 Hz), 3.67–3.79(4H, m), 4.04(3H, s), 4.37(2H, t, J=6.6 Hz), 6.73 (1H, dd, J=1.5, 8.0 Hz), 6.86(1H, dt, J=1.5, 8.0 Hz), 7.05 (1H, dd, J=1.5, 8.0 Hz), 7.10(1H, dt, J=1.5, 8.0 Hz), 7.45 (2H, d, J=8.6 Hz), 7.81 (2H, d, J=8.6 Hz), 8.01 (1H, s)

Example 13

Synthesis of N-(2-isopropylphenyl)-3-[6-(4-t-butylphenylsulfonylamino)-2-(4-formylpiperazinyl)-5-(2-methoxyphenoxy)-4-pyrimidinyloxy]-propionamide The procedure described in Example 2 was repeated by use of 3-[6-(4-t-butylphenylsulfonylamino)-2-(4-formylpiperazinyl)-5-(2-methoxyphenoxy)-4-pyrimidinyloxy]propionic acid and 2-isopropylaniline, to thereby obtain the title compound as a colorless solid.

$^1$H-NMR(CDCl$_3$, ppm, TMS): 1.10(6H, d, J=7.1 Hz), 1.32(9H, s), 2.77(2H, t, J=5.7 Hz), 2.89(1H, sep, J=7.1 Hz), 3.26(2H, brs), 3.45(2H, brs), 3.57–3.79(4H, br), 3.94(3H, s), 4.68(2H, t, J=5.7 Hz), 6.68(1H, m), 6.82–7.29(7H, m), 7.46(2H, d, J=8.3 Hz), 7.82(2H, d, J=8.3 Hz), 8.09(1H, s)

Synthesis Example 15

Synthesis of 4-t-butyl-N-[2-(4-t-butoxycarbonylpiperazinyl)-6-(3-hydroxypropyloxy)-5-(2-methoxyphenoxy)-4-pyrimidinyl] benzenesulfonamide 4-t-Butyl-N-[6-(3-hydroxypropyloxy)-5-(2-methoxyphenoxy)-2-piperazinyl-4-pyrimidinyl]-benzenesulfonamide (55 mg; 0.096 mmol)) was dissolved in chloroform (2 ml). N,N-Dimethylaminopyridine (1.5 mg; 0.01 mmol) and di-t-butyldicarbonate (21.8 mg; 0.1 mmol) were added to the solution. The resultant mixture was stirred overnight at room temperature, and then poured into water, and extracted with chloroform. The organic layer was washed with water, dried over anhydrous sodium sulfate, and evaporated. The residue was purified by silica gel column chromatography (chloroform:methanol=10:1), to thereby obtain 61 mg (yield: 94%) of the title compound as a pale yellow oil.

$^1$H-NMR(CDCl$_3$, ppm, TMS): 1.33(9H, s), 1.48(9H, s), 1.86–1.94(2H, m), 3.35(4H, brs), 3.52–3.61(6H, m), 4.01 (3H, s), 4.42(2H, t, J=6.1 Hz), 6.84(1H, dt, J=1.7, 8.1 Hz), 6.95(1H, dd, J=1.7, 8.1 Hz), 6.99(1H, dd, J=1.7, 8.1 Hz), 7.08(1H, dt, J=1.7, 8.1 Hz), 7.47(2H, d, J=8.5 Hz), 7.86(2H, d, J=8.5 Hz) IR(KBr)cm$^{-1}$: 3020, 2401, 1522, 1212, 1047

Example 14

Synthesis of 3-[2-(4-t-butoxycarbonyl-piperazinyl)-6-(4-t-butylphenyl-sulfonylamino)-5-(2-methoxyphenoxy)-4-pyrimidinyloxy]propionic acid The procedure described in Example 1 was repeated by use of 4-t-butyl-N-[2-(4-t-butoxycarbonylpiperazinyl)-6-(3-hydroxypropyloxy)-5-(2-methoxyphenoxy)-4-pyrimidinyl]-benzenesulfonamide, to thereby obtain the title compound as a pale yellow oil.

$^1$H-NMR(CDCl$_3$, ppm, TMS): 1.33(9H, s), 1.48(9H, s), 2.75(2H, t, J=6.4 Hz), 3.34(4H, brs), 3.56(4H, brs), 4.01(3H, s), 4.53(2H, t, J=6.4 Hz), 6.82(1H, t, J=7.1 Hz), 6.94–7.06 (3H, m), 7.46(2H, d, J=8.8 Hz), 7.85(2H, d, J=8.8 Hz)

Example 15

Synthesis of N-(2-isopropylphenyl)-3-[2-(4-t-butoxycarbonylpiperazinyl)-6-(4-t-butylphenylsulfonylamino)-5-(2-methoxyphenoxy)-4-pyrimidinyloxy]-propionamide The procedure described in Example 2 was repeated by use of 3-[2-(4-t-butoxycarbonylpiperazinyl)-6-(4-t-butyl-phenylsulfonylamino)-5-(2-methoxyphenoxy)-4-pyrimidinyloxy]-propionic acid and 2-isopropylaniline, to thereby obtain the title compound as a pale yellow oil.

$^1$H-NMR(CDCl$_3$, ppm, TMS): 1.10(6H, d, J=6.8 Hz), 1.33(9H, s), 1.48(9H, S), 2.77(2H, t, J=6.4 Hz), 2.89(1H, sep, J=6.8 Hz), 3.33(4H brs), 3.58(4H, brs), 3.92(3H, s), 4.67(2H, t, J=6.4 Hz), 6.69(1H, m), 6.89–7.25(7H, m), 7.45(2H, d, J=8.3 Hz), 7.83(2H, d, J=8.3 Hz)

Example 16

Synthesis of N-(1-phenylethyl)-[6-(4-t-butylphenylsulfonylamino)-2-(4-formylpiperazinyl)-5-(2-methoxyphenoxy)-4-pyrimidinyloxy]-acetamide N-(1-Phenylethyl)-hydroxyacetamide (50 mg, 0.3 mmol) was dissolved in dimethyl sulfoxide (0.56 ml). Sodium (11.5 mg; 0.5 mmol) was added to the solution, and the resultant mixture was stirred at room temperature for two hours. 4-t-Butyl-N-[6-chloro-2-(4-formylpiperazinyl)-5-(2-methoxyphenoxy)-4-pyrimidinyl]benzenesulfonamide (56 mg; 0.1 mmol) was added thereto, and the resultant mixture was stirred for 1 hour at 120° C., then poured into water, made acidic with hydrochloric acid, and extracted with ethyl acetate. The extracted was washed with water, dried over anhydrous sodium sulfate, and evaporated. The residue was purified by silica gel column chromatography (chloroform:methanol=20:1), to thereby obtain 23.8 mg (yield: 34%) of the title compound as a pale yellow oil.

$^1$H-NMR(CDCl$_3$, ppm, TMS): 1.18(3H, d, J=7.1 Hz), 1.22(9H, s) 3.04–3.12(2H, m), 3.26–3.35(2H, m), 3.37–3.49 (4H, m), 3.80(3H, s), 4.58(2H, s), 4.97(1H, m), 6.63–6.73 (2H, m), 6.84(1H, dd, J=1.5, 7.8 Hz), 6.89–6.98(3H, m), 7.03–7.11(3H, m), 7.39(2H, d, J=8.5 Hz), 7.77(2H, d, J=8.5 Hz), 7.96(1H, s)

Example 17

Synthesis of N-(2-ethylphenyl)-3-[6-(4-t-butylphenylsulfonylamino)-5-(2-methoxyphenoxy)-2-morpholino-4-pyrimidinyloxy]propionamide The procedure described in Example 2 was repeated by use of 3-[6-(4-t-butylphenylsulfonylamino)-5-(2-methoxyphenoxy)-2-morpholino-4-pyrimidinyloxy] propionic acid and 2-ethylaniline, to thereby obtain the title compound as a colorless oil.

$^1$H-NMR(CDCl$_3$, ppm, TMS): 1.08(3H, t, J=7.6 Hz), 1.32(9H, s), 2.41(2H, q, J=7.6 Hz), 2.74(2H, t, J=5.7 Hz), 3.60(8H, m), 3.88(3H, s), 4.64(2H, t, J=5.7 Hz), 6.66(1H, m), 6.85–6.94(2H, m), 7.14–7.26(4H, m), 7.44(2H, d, J=8.8 Hz), 7.59(1H, d, J=7.8 Hz), 7.82(2H, d, J=8.8 Hz), 8.65(1H, brs) IR(KBr)cm$^{-1}$: 2970, 1670, 1615, 1560, 1500, 1440, 1340, 1250, 1170, 1110, 1080, 750

Example 18

Synthesis of N-(2,6-dimethylphenyl)-3-[6-(4-t-butylphenylsulfonylamino)-5-(2-methoxyphenoxy)-2-morpholino-4-pyrimidinyloxy]propionamide The procedure described in Example 3 was repeated by use of 3-[6-(4-t-butylphenylsulfonylamino)-5-(2-methoxyphenoxy)-2-morpholino-4-pyrimidinyloxy] propionic acid and 2,6-dimethylaniline, to thereby obtain the title compound as a colorless oil.

$^1$H-NMR(CDCl$_3$, ppm, TMS): 1.33(9H, s), 2.02(6H, s), 2.71(2H, t, J=5.7 Hz), 3.65(8H, m), 3.67(3H, s), 4.61(2H, t, J=5.7 Hz), 6.67–6.73(2H, m), 6.81–6.85(2H, m), 6.88–7.09 (3H, m), 7.45(2H, d, J=8.8 Hz), 7.85(2H, d, J=8.8 Hz), 8.45(1H, brs) IR(KBr)cm$^{-1}$: 2965, 1670, 1595, 1565, 1500, 1440, 1335, 1250, 1170, 1115, 1085, 760

Example 19

Synthesis of N-(2-methoxyphenyl)-3-[6-(4-t-butylphenylsulfonylamino)-5-(2-methoxyphenoxy)-2-morpholino-4-pyrimidinyloxy]propionamide The procedure described in Example 2 was repeated by use of 3-[6-(4-t-butylphenylsulfonylamino)-5-(2-methoxyphenoxy)-2-morpholino-4-pyrimidinyloxy] propionic acid and 2-methoxyaniline, to thereby obtain the title compound as a colorless oil.

$^1$H-NMR(CDCl$_3$, ppm, TMS): 1.29(9H, s), 2.40(2H, t, J=6.1 Hz), 3.56(8H, m), 3.70(3H, s), 3.93(3H, s), 4.62(2H, t, J=6.1 Hz), 6.55(1H, m), 6.78(1H, d, J=8.1 Hz), 6.80–7.01 (5H, m), 7.31(2H, d, J=8.6 Hz), 7.78(2H, d, J=8.6 Hz), 7.83(1H, m), 8.28(1H, d, J=7.8 Hz) IR(KBr)cm$^{-1}$: 2965, 1685, 1600, 1560, 1500, 1440, 1335, 1250, 1170, 1115, 1085, 750

Example 20

Synthesis of N-(4-isopropylphenyl)-3-[6-(4-t-butylphenylsulfonylamino )- 5-(2-methoxyphenoxy) -2-morpholino-4-pyrimidinyloxy]propionamide The procedure described in Example 2 was repeated by use of 3-[6-(4-t-butylphenylsulfonylamino)-5-(2-methoxyphenoxy )-2-morpholino-4-pyrimidinyloxy] propionic acid and 4-isopropylaniline, to thereby obtain the title compound as a colorless oil.

$^1$H-NMR(CDCl$_3$, ppm, TMS): 1.22(6H, d, J=6.8 Hz), 1.32(9H, S), 2.66(2H, t, J=5.9 Hz), 2.86(1H, sep, J=6.8 Hz), 3.50–3.65(8H, m), 3.86(3H, s), 4.59(2H, t, J=5.9 Hz), 6.63 (1H, dt, J=7.7, 1.5 Hz), 6.81–6.98(3H, m), 7.11(2H d, J=8.5 Hz), 7.27(2H, d, J=8.5 Hz), 7.43(2H, d, J=8.8 Hz), 7.82(2H, d, J=8.8 Hz), 8.7(1H, brs) IR(KBr)cm$^{-1}$: 2960, 1690, 1615, 1560, 1495, 1440, 1340, 1250, 1170, 1110, 1085, 750

Example 21

Synthesis of N-(3-isopropylphenyl)-3-[6-(4-t-butylphenylsulfonylamino)-5-(2-methoxyphenoxy)-2-morpholino-4-pyrimidinyloxy]propionamide The procedure described in Example 2 was repeated by use of 3-[6-(4-t-butylphenylsulfonylamino)-5-(2-methoxyphenoxy)-2-morpholino-4-pyrimidinyloxy] propionic acid and 3-isopropylaniline, to thereby obtain the title compound as a colorless oil.

$^1$H-NMR(CDCl$_3$, ppm, TMS) 1.21 (6H, d, J=7.1 Hz), 1.32(9H, s), 2.69(2H, t, J=6.0 Hz), 2.84(1H, sep, J=7.1 Hz), 3.50–3.65(8H, m), 3.93(3H, s), 4.62(2H, t, J=6.0 Hz), 6.64 (1H, dt, J=7.6, 1.5 Hz), 6.85–7.01 (4H, m), 7.14–7.22(2H, m), 7.30(1H, brs), 7.43(2H, d, J=8.8 Hz), 7.82(2H, d, J=8.8 Hz), 8.72(1H, brs) IR(KBr)cm$^{-1}$: 2965, 1700, 1615, 1560, 1495, 1440, 1340, 1250, 1170, 1115, 1085, 755

Example 22

Synthesis of methyl 3-[6-(4-t-butylphenylsulfonylamino)-5-(2-methoxyphenoxy)-2-morpholino-4-pyrimidinyloxy]propionate Methanol (0.5 ml) and concentrated sulfuric acid (two droplets) were added to 3-[6-(4-t- butylphenylsulfonylamino)-5-(2-methoxyphenoxy)-2-morpholino-4-pyrimidinyloxy]propionic acid (50 mg), and the mixture was stirred for 4 hours at room temperature, then poured into water, and extracted with ethyl acetate. The extract was washed successively with water and brine, dried over anhydrous sodium sulfate, and concentrated under reduced pressure. The residue was purified by silica gel preparative thin layer chromatography (chloroform-methanol (30:1)), to thereby obtain 46 mg (yield: 90%) of the title compound as a colorless oil.

$^1$H-NMR(CDCl$_3$, ppm, TMS): 1.32(9H, s), 2.71(2H, t, J=6.4 Hz), 3.62(3H, s), 3.52–3.69(8H, m), 4.02(3H, s), 4.54(2H, t, J=6.4 Hz), 6.84(1H, ddd, J=8.1, 7.3, 1.5 Hz), 6.99(1H, dd, J=8.1, 1.5 Hz), 7.00 (1H, dd, J=8.1, 1.5 Hz), 7.08(1H, ddd, J=8.1, 7.3, 1.5 Hz), 7.44(2H, d, J=8.8 Hz), 7.84(2H, d, J=8.8 Hz), 8.70(1H, brs) IR(KBr)cm$^{-1}$: 2965, 1740, 1615, 1560, 1500, 1440, 1340, 1250, 1170, 1115, 1085, 750

Example 23

Synthesis of benzyl 3-[6-(4-t-butylphenylsulfonylamino)-5-(2-methoxyphenoxy)-2-morpholino-4-pyrimidinyloxy]propionate The procedure described in Example 22 was repeated by use of 3-[6-(4-t-butylphenylsulfonylamino)-5-(2-methoxyphenoxy)-2-morpholino-4-pyrimidinyloxy] propionic acid and benzyl alcohol, to thereby obtain the title compound as a colorless oil.

$^1$H-NMR(CDCl$_3$, ppm, TMS): 1.32(9H, s), 2.75(2H, t, J=6.4 Hz), 3.62(3H, S), 3.50–3.65(8H, m), 4.01 (3H, s), 4.56(2H, t, J=6.4 Hz), 5.04(2H, S), 6.80(1H, ddd, J=8.1, 7.3, 1.5 Hz), 6.97(1H, dd, J=8.3, 1.5 Hz), 6.98(1H, dd, J=8.1, 1.5 Hz), 7.06(1H, ddd, J=8.3, 7.3, 1.5 Hz), 7.30(5H, m), 7.44 (2H, d, J=8.5 Hz), 7.84(2H, d, J=8.5 Hz), 8.70(1H, brs) IR(KBr)cm$^{-1}$: 2965, 1740, 1595, 1500, 1440, 1340, 1250, 1170, 1110, 1085, 750

Test Example 1

Endothelin binding inhibition experiment

Preparation of crude receptor membrane samples (ET$_A$) from smooth muscles of porcine thoracic aorta:

Porcine thoracic aorta which was separated from the fatty tissue and then was removed endothelium with gauze was minced, and then homogenized in three times the volume of Tris-HCl buffer (pH 7.4) (buffer A) containing 0.25M sucrose, 3 mM ethylenediaminetetraacetic acid, 5 μg/ml of aprotinin, 10 μg/ml of pepstatin A, 10 μg/ml of leupeptin, and 0.1 μM p-amidinophenylmethanesulfonyl fluoride. After centrifugation for 30 minutes at 1,000×g, the supernatant was further centrifuged for 30 minutes at 100,000×g. The pellets were suspended in buffer A, and recentrifuged for 30 minutes at 100,000×g. The pellets were suspended in buffer A and the suspension was stored at −80° C. $^{125}$I-Endothelin-1 binding assay:

The thus-obtained membrane sample (1 μl) was incubated together with $^{125}$I-endothelin-1 (2×10$^{-11}$M) and various concentrations of the compounds, for 2 hours at 25° C., in 250 μl in total volume of 50 mM Tris-HCl buffer (pH 7.4) containing 0.5% bovine serum albumin. The incubated mixture was filtered by use of HVPP filters (pore size 0.45 μm, product of Milipore). The filters were washed with cold buffer A four times, and then measured with a gamma-ray counter (Aroka Autowell Gamma System ARC-251). Preparation of crude receptor membrane samples (ET$_B$) from rat brain and assay of $^{125}$I endothelin-1:

Rat brain tissue was minced, and a crude receptor membrane sample was prepared in a manner similar to that used in the aforementioned case of porcine thoracic aorta. Also, $^{125}$I-endothelin-1 assay was performed in the same manner as described above.

The results of the thus-performed endothelin binding inhibition experiment for each of the two receptors are shown in Table 2.

TABLE 3

| Compound | IC50 (μM) | |
|---|---|---|
| (Example No.) | ETA | ETB |
| 2 | 0.063 | 0.00086 |
| 3 | 0.032 | 0.029 |
| 13 | 0.068 | 0.0054 |
| 23 | 0.24 | 0.0051 |

Industrial Applicability

The novel pyrimidine derivatives (1) of the present invention exhibit strong binding inhibitory activity against endothelin having very strong vasoconstrictive effect. Therefore, the compounds are effective as remedies for various endothelin-related diseases including heart diseases such as ischemic heart infarction, congestive heart failure, arrhythmia, and unstable angina; airway diseases such as asthma; hypertonia such as pulmonary hypertension and renal hypertension; hypofunctions of organs which may occur in association with operation or transplantation; subarachnoid hemorrhage; post-PTCA reconstriction; circulatory diseases such as vasospasm; kidney diseases such as acute and chronic renal failure; diseases that are accompanied by vascular lesion such as diabetes and hyperlipemia; arteriosclerosis; liver diseases such as alcohol-induced liver disorders; gastrointestinal disorders such as those of gastric mucosa; other bone diseases; prostatic hypertrophy; and urinary disorders.

We claim:

1. A pyrimidine derivative of the following formula (1) or a pharmaceutically acceptable salt of the derivative:

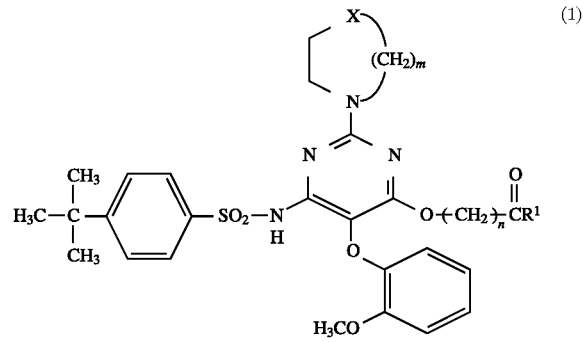

wherein R' represents a hydroxyl group, a lower alkoxy group, a phenyloxy group which may have a substituent, an aralkyloxy group which may have a substituent, or —NR$^2$R$^3$; X represents an oxygen atom or N—R$^4$; m is 2 or 3; and n is 1 or 2; wherein each of R$^2$ and R$^3$, which are identical to or different from each other, represents a hydrogen atom, a hydroxyl group, a lower alkyl group which may have a substituent, a phenyl group which may have a substituent, an aralkyl group which may have a substituent, or a heterocyclic group which may have a substituent; R$^4$ represents a lower alkyl group, a phenyl group, a formyl group, or a lower alkoxycarbonyl group.

2. The pyrimidine derivative or a pharmaceutically acceptable salt of the derivative according to claim 1, where m is 2.

3. The pyrimidine derivative or a pharmaceutically acceptable salt of the derivative according to claim 1, where m is 3.

4. A pharmaceutical composition comprising an effective amount as endothelin antagonist of the pyrimidine derivative or a pharmaceutically acceptable salt of the derivative according to claim 1 and pharmaceutically acceptable carrier.

5. The pharmaceutical composition according to claim 4, wherein in the derivative of formula (1) m is 2.

6. The pharmaceutical composition according to claim 4, wherein in the derivative of formula (1) m is 3.

7. A method for preventing or treating a disease induced by endothelin, comprising administering to a subject an effective amount therefor of the pyrimidine derivative or pharmaceutically acceptable salt of the pyrimidine derivative according to claim 1.

8. The method according to claim 7, where the disease induced by endothelin is a circulatory disease.

9. The method according to claim 7, wherein in the derivative of formula (1) m is 2.

10. The method according to claim 1, wherein in the derivative of formula (1) m is 3.

11. The method according to claim 8, wherein in the derivative of formula (1) m is 2.

12. The method according to claim 8, wherein in the derivative of formula (1) m is 3.

* * * * *